(12) United States Patent
Kotter et al.

(10) Patent No.: US 8,173,855 B2
(45) Date of Patent: May 8, 2012

(54) PROCESS FOR THE PRODUCTION OF LOW-CONCENTRATION ETHYLENE FOR CHEMICAL USE

(75) Inventors: Joachim Kotter, Markkleeberg (DE); Hans-Dieter Winkler, Leipzig (DE); Peter Mews, Mittweida (DE); Michel Lempereur, Corbais (BE); Dominique Balthasart, Brussels (BE); Michel Strebelle, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 14 days.

(21) Appl. No.: 12/995,509

(22) PCT Filed: May 28, 2009

(86) PCT No.: PCT/EP2009/056577
§ 371 (c)(1), (2), (4) Date: Dec. 1, 2010

(87) PCT Pub. No.: WO2009/147076
PCT Pub. Date: Dec. 10, 2009

(65) Prior Publication Data
US 2011/0077439 A1 Mar. 31, 2011

(30) Foreign Application Priority Data
Jun. 3, 2008 (EP) .................................. 08157514

(51) Int. Cl.
*C07C 7/04* (2006.01)
(52) U.S. Cl. ........ 585/809; 585/802; 585/329; 585/330; 585/324
(58) Field of Classification Search .................... None
See application file for complete search history.

(56) References Cited

U.S. PATENT DOCUMENTS
2,588,323 A * 3/1952 Kniel ............................ 585/650
(Continued)

FOREIGN PATENT DOCUMENTS
DE 1518827 A1 8/1969
(Continued)

OTHER PUBLICATIONS
U.S. Appl. No. 11/722,603, Michel Strebelle, et al, Nov. 2, 2007.
(Continued)

*Primary Examiner* — Tam M Nguyen
(74) *Attorney, Agent, or Firm* — Beatrice C. Ortego

(57) ABSTRACT

Process for the production of ethylene for chemical use starting with a hydrocarbon source according to which: a) the hydrocarbon source is subjected to a first cracking step, namely a pyrolysis step carried out in a cracking oven, thus producing a mixture of cracking products; b) the mixture of cracking products is subjected to a succession of treatment steps, including a compression step, which makes it possible to obtain a purified crude gas stream; c) the purified crude gas stream is then cooled to a temperature where hydrocarbons with 6 and more carbon atoms condense so that they can be removed from the purified crude gas stream; d) the resulting purified gas stream is afterwards supplied to one separating column, where a fraction A containing hydrogen, methane and ethylene is separated at the head of the column and a heavy fraction C is separated at the bottom of the column; e) a part of the reflux of this column is supplied to a refrigeration cycle leading to a fraction B enriched with ethylene; and f) the fraction A and fraction B are separately supplied to chemical use of ethylene.

10 Claims, 1 Drawing Sheet

U.S. PATENT DOCUMENTS

| | | | | |
|---|---|---|---|---|
| 2,804,488 | A * | 8/1957 | Cobb, Jr. | 585/650 |
| 3,444,696 | A * | 5/1969 | Jacobs et al. | 62/623 |
| 3,485,886 | A * | 12/1969 | Mitchell et al. | 585/652 |
| 4,548,706 | A | 10/1985 | Papadopoulos et al. | |
| 4,743,282 | A * | 5/1988 | Mehra | 62/625 |
| 4,900,347 | A * | 2/1990 | McCue et al. | 62/627 |
| 5,082,481 | A | 1/1992 | Barchas et al. | |
| 5,421,167 | A * | 6/1995 | Verma | 62/631 |
| 5,453,559 | A * | 9/1995 | Phillips et al. | 585/809 |
| 5,746,066 | A | 5/1998 | Manley | |
| 6,037,515 | A | 3/2000 | Wimmer | |
| 6,405,561 | B1 * | 6/2002 | Mortko et al. | 62/631 |
| 6,441,263 | B1 * | 8/2002 | O'Rear et al. | 585/650 |
| 6,900,363 | B2 | 5/2005 | Harth et al. | |
| 7,294,749 | B2 * | 11/2007 | Verma et al. | 585/809 |
| 7,429,686 | B2 * | 9/2008 | Verma et al. | 585/809 |
| 2006/0004242 | A1 | 1/2006 | Verma et al. | |
| 2008/0141712 | A1 * | 6/2008 | Verma | 62/620 |

FOREIGN PATENT DOCUMENTS

| | | |
|---|---|---|
| EP | 872537 B1 | 10/1998 |
| GB | 846679 A | 8/1960 |
| GB | 1149093 A | 4/1969 |
| WO | WO 03048088 A1 | 6/2003 |
| WO | WO 2006067188 A1 | 6/2006 |
| WO | WO 2006067190 A1 | 6/2006 |
| WO | WO 2006067191 A1 | 6/2006 |
| WO | WO 2006067192 A1 | 6/2006 |
| WO | WO 2006067193 A1 | 6/2006 |
| WO | WO 2007018510 A1 | 2/2007 |
| WO | WO 2007147870 A1 | 12/2007 |
| WO | WO 2008000693 A1 | 1/2008 |
| WO | WO 2008000702 A1 | 1/2008 |
| WO | WO 2008000705 A1 | 1/2008 |
| WO | WO 2008076206 A1 | 6/2008 |
| WO | WO 2009106479 A1 | 12/2009 |
| WO | WO 2009147083 A1 | 12/2009 |
| WO | WO 2009147100 A1 | 12/2009 |
| WO | WO 2009147101 A1 | 12/2009 |

OTHER PUBLICATIONS

U.S. Appl. No. 11/722,589, Dominique Balthasart, et al, Oct. 18, 2007.
U.S. Appl. No. 11/722,598, Michel Strebelle, et al, Oct. 15, 2007.
U.S. Appl. No. 11/722,607, Michel Strebelle, et al, Jun. 22, 2007.
U.S. Appl. No. 11/722,587, Michel Strebelle, et al, Oct. 17, 2007.
U.S. Appl. No. 12/304,297, Dominique Balthasart, et al, Dec. 11, 2008.
U.S. Appl. No. 12/304,329, Michel Strebelle, et al, Dec. 11, 2008.
U.S. Appl. No. 12/304,379, Dominique Balthasart, et al, Dec. 11, 2008.
U.S. Appl. No. 12/304,434, Michel Strebelle, et al, Dec. 11, 2008.
U.S. Appl. No. 12/919,101, Andre Peitijean, et al, Aug. 24, 2010.
U.S. Appl. No. 12/995,486, Michel Lempereur, et al, Dec. 1, 2010.
U.S. Appl. No. 12/995,518, Andre Petitjean, et al, May 29, 2009.
U.S. Appl. No. 12/995,539, Michel Lempereur, et al, Dec. 1, 2010.

* cited by examiner

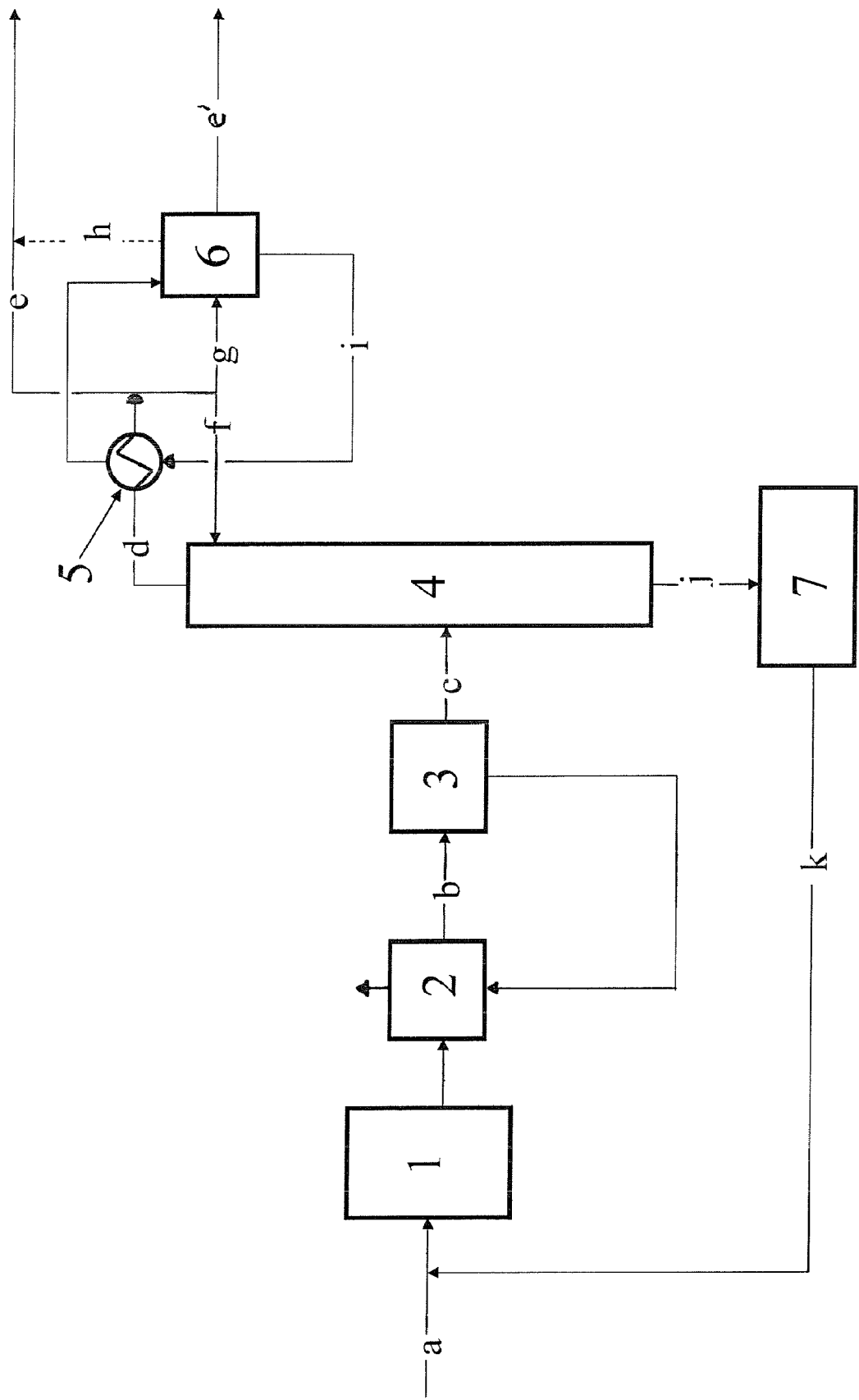

PROCESS FOR THE PRODUCTION OF LOW-CONCENTRATION ETHYLENE FOR CHEMICAL USE

CROSS-REFERENCE TO RELATED APPLICATIONS

The present patent application is a U.S. national stage application under 35 U.S.C. §371 of International Application No. PCT/EP2009/056577 filed May 28, 2009 which claims the benefit of the European patent application No. 08157514.4 filed on Jun. 3, 2008, the content of this application being incorporated herein by reference for all purposes.

TECHNICAL FIELD

The present invention relates to a process for the production of low-concentration ethylene for chemical use.

BACKGROUND

To date, ethylene which is more than 99.8% pure is usually used for chemical synthesis. This ethylene of very high purity is obtained via the cracking of various petroleum products, followed by numerous complex and expensive separation operations in order to isolate the ethylene from the other products of cracking and to obtain a product of very high purity.

In conventional ethylene plants, as described for example in the patent EP 0872537 B1, the crude gas compression is followed by a complicated separation process, in which ethylene and propylene of high purity (polymer quality) are produced. Further products may be butadiene, benzene, toluene, styrene and others. The separation process is characterized by the following steps:
1. Splitting in C2 minus fraction/C3 plus fraction
2. Splitting of the C2 minus fraction:
   2.1. Separation of hydrogen and methane in a deep cooling at approximately −150° C.
   2.2. Separation of a C2 fraction
   2.3. Splitting of the C2 fraction in ethylene and ethane
   2.4. Recycling of ethane to cracking
3. Splitting of C3 plus fraction into a C3 and a C4 plus fraction:
   3.1 Hydrogenation of propyne and propadiene in the C3 fraction
   3.2. Distillation of pure propylene from the C3 fraction
   3.3. Splitting of the C4/C5 fraction, depending upon the requirements.

Integrated into the plant for production of ethylene are refrigeration units to generate temperatures down to −150° C. Pure ethylene and pure propylene serve as refrigerating medium.

For the chemical use of ethylene, a high concentration of >98% is in many cases not necessary.

The patent application WO 03/048088 describes the production of low-concentration ethylene for the chemical reaction with chlorine by means of ethane dehydrogenation. The ethane-loaded gas stream contains not only hydrogen and methane, but also high amounts of unconverted ethane. For the economic design of the process, the unconverted ethane must be fed back to ethane dehydrogenation after complicated cleaning processes. This process can only use ethane as feedstock. A significant disadvantage is the very low concentration of ethylene—less than 60%—as well as the fact that further components of the gas stream such as hydrogen, propylene, butadiene only allow to use the ethylene in very special processes.

In the patent application WO 2006/067188, the production of vinyl chloride is described, starting with the cracking of ethane/liquefied gas as feedstock. The feedstock undergoes the usual cracking. After quenching and water washing, the cracked gas is compressed and cleaned from hydrogen sulfide, carbon dioxide and water, before it is split into three fractions. Fraction A contains ethylene, ethane, methane, hydrogen as well as small amounts of carbon monoxide. Fraction B contains mainly ethylene and ethane as well as small amounts of methane and very low amounts of hydrogen. Both fractions are used for the reaction with chlorine in various processes. A fraction C contains ethane and hydrocarbons with more than 3 carbon atoms. For the separation of a gas mixture, various circuits of at least two columns are described.

For the use of fraction C, various variants are suggested, such as combustion, recycling as feedstock without further treatment or recycling to the feedstock after hydrogenation of unsaturated components contained in fraction C. In accordance with our experiences, the recycling to feedstock without further treatment is only a hypothetic variant, since feedstock with high olefin contents leads to strong coke formation in the pyrolysis furnaces and gives a very low ethylene yield.

Prior to the hydrogenation of fraction C, the splitting into fractions with less or more than 5 carbon atoms is described. Only the fraction with 5 and less carbon atoms undergoes hydrogenation. The description does not contain information on the technology of hydrogenation.

The hydrogenation of propylene is specified in patent application DE 1518827. This patent application describes the hydrogenation of propylene into propane to be returned as feedstock to the cracking furnaces for ethylene production. Hydrogenation takes place in a reactor in a hydrogen atmosphere in the liquid phase (trickle phase reactor). Such reactors and the utilized catalysts based on metals of the eighth subgroup (palladium, platinum) have proven themselves internationally for the hydrogenation of liquid unsaturated hydrocarbons. It is explicitly said that the cracking of unsaturated hydrocarbons leads to increased coke formation.

SUMMARY

The purpose of the invention is to provide a technologically simpler and more cost-effective process for producing ethylene for chemical use, in which the accumulation of by-products is eliminated.

To this effect, the invention relates to a process for the production of ethylene for chemical use starting with a hydrocarbon source according to which:
a) the hydrocarbon source is subjected to a first cracking step, namely a pyrolysis step carried out in a cracking oven, thus producing a mixture of cracking products;
b) the mixture of cracking products is subjected to a succession of treatment steps, including a compression step, which makes it possible to obtain a purified crude gas stream;
c) the purified crude gas stream is then cooled to a temperature where hydrocarbons with 6 and more carbon atoms condense so that they can be removed from the purified crude gas stream;
d) the resulting purified gas stream is afterwards supplied to one separating column, where a fraction containing hydrogen, methane and ethylene (fraction A) is separated at the head of the column and a heavy fraction (fraction C) is separated at the bottom of the column;

e) a part of the reflux of this column is supplied to a refrigeration cycle leading to a fraction enriched with ethylene (fraction B); and f) fraction A and fraction B are separately supplied to chemical use of ethylene.

BRIEF DESCRIPTION OF THE DRAWING

For a detailed description, reference will now be made to the accompanying drawing in which:

FIG. 1 schematically represents the preferred embodiment of the process according to the invention.

DETAILED DESCRIPTION

The process according to the invention is a process starting with a hydrocarbon source (also called feedstock).

The hydrocarbon source considered may be any known hydrocarbon source. Preferably, the hydrocarbon source subjected to cracking (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane, butane and propane/butane mixtures. In a more particularly preferred manner, the hydrocarbon source is chosen from the group consisting of propane, butane and propane/butane mixtures. The propane/butane mixtures may exist as such or may consist of mixtures of propane and butane.

The expression ethane, propane, butane and propane/butane mixtures is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

In the process for the production of ethylene for chemical use according to the present invention, the hydrocarbon source is subjected to a first cracking step, namely a pyrolysis step carried out in a cracking oven, thus producing a mixture of cracking products.

The expression first cracking step, namely a pyrolysis step carried out in a cracking oven (step a)), is understood to mean a conversion, under the action of heat, of the hydrocarbon source in the presence or absence of third compounds such as water, oxygen, a sulfur derivative and/or a catalyst so as to give rise to the formation of a mixture of cracking products.

This mixture of cracking products advantageously comprises hydrogen, carbon monoxide, carbon dioxide, nitrogen, oxygen, hydrogen sulfide, organic compounds comprising at least one carbon atom and water.

After step a) defined above, according to step b), the mixture of cracking products is subjected to a succession of treatment steps, including a compression step, which makes it possible to obtain a purified crude gas stream.

The first cracking step a) is advantageously followed by step b) consisting of a succession of treatment steps among which are the steps for thermal recovery of the heat of the cracked gas, optionally organic quenching (optionally including recovery of heat through a succession of exchangers with intermediate fluids), aqueous quenching, compression and drying of the gas, alkaline washing aimed at removing at least the majority of the carbon dioxide, optionally hydrogenating the undesirable derivatives such as, for example, acetylene (to achieve advantageously a value of approximately 5 ppm of acetylene), optionally removing part of the hydrogen and/or the methane and removing hydrogen sulfide.

After step b) defined above, according to step c), the purified crude gas stream is then cooled to a temperature where hydrocarbons with 6 and more carbon atoms condense so that they can be removed from the purified crude gas stream.

The temperature to be selected depends upon the gas composition and the gas pressure. The temperature selection is advantageously such that the benzene content in the gas after the cooling amounts to advantageously less than about 2, preferably less then about 1 and more preferably less than about 0.5% by weight.

The purified crude gas stream is preferably cooled to a temperature of advantageously at most 5, preferably at most 0 and more preferably at most $-5°$ C. It is preferably cooled to a temperature of advantageously at least $-30$, preferably at least $-25$ and more preferably at least $-20°$ C.

The hydrocarbons condensed in step c) are returned advantageously to step b), preferably to the compression step of step b), more preferably to the last stage of compression of the compression step of step b).

After step c) defined above, according to step d), the resulting purified gas stream is afterwards supplied to one separating column, where a fraction containing hydrogen, methane and ethylene (fraction A) is separated in the head of the column and a heavy fraction (fraction C) is separated at the bottom of the column The purified gas stream is supplied to one column, preferably after having been cooled further, where the separation of ethylene and ethane advantageously takes place. Ethylene, methane and hydrogen are advantageously extracted from the head of the column. All other gas components are advantageously contained in the bottom product. The ethylene contained in the gaseous head product (fraction A) is supplied to a chemical use of ethylene.

The separation of ethane and ethylene is advantageously possible, despite of the presence of hydrogen, methane and higher hydrocarbons, provided that suitable technological conditions in this column are chosen. Ethylene, methane and hydrogen are separated in the head of column (fraction A), all other components contained in the crude gas remain in the bottom product of the column (fraction C).

The column is advantageously equipped with a condenser for condensation of the head product, a tank for condensed head product, a boiler for heating the column as well as relevant pumps. Liquid ethylene is preferably used for the condensation of the head product that is produced in an ethylene refrigerator.

The pressure of the column is advantageously adjusted to ensure that the condensation of the head product is possible, preferably by means of liquid ethylene. The pressure is advantageously of at least 8, preferably of at least 10 and more preferably of at least 12 bars. The pressure is advantageously of at most 45, preferably of at most 40 and more preferably of at most 38 bars.

The temperature is advantageously at least $-100$, preferably at least $-90$ and more preferably at least $-80°$ C. at the top of column. It is advantageously at most $-30$, preferably at most $-40$ and more preferably at most $-50°$ C. at the top of column.

In this column, ethylene/ethane separation is advantageously done mainly in the upper part of the column, while the separation of C3 and higher-boiling hydrocarbons is made in the lower part of the column.

After step d) defined above, according to step e), a part of the reflux of the separating column is supplied to a refrigeration cycle leading to a fraction enriched with ethylene (fraction B).

A part of the reflux is supplied to a refrigeration cycle, preferably after evaporation and utilization of the refrigeration content. The refrigeration cycle is preferably based on ethylene.

This amount of the part of the reflux supplied to the refrigeration cycle is advantageously taken from the refrigeration cycle in gaseous state and represents a mainly hydrogen-free, more concentrated ethylene fraction which is supplied for chemical use of ethylene (product B).

The liquid produced by the cooling of the head product of the column serves advantageously as reflux to the column. The liquid produced by the cooling of the head product of the column is advantageously introduced in the refrigeration cycle, where it is mixed with the liquefied ethylene of the refrigeration cycle. The liquid ethylene is more preferably supplied to the head product condenser and evaporates. After the evaporation, the ethylene again most preferably enters the ethylene refrigeration cycle, where it is compressed by means of a compressor, before it is liquefied. This approach allows for the complete recovery of the cooling content of the liquid produced by the cooling of the head product of the column supplied to the ethylene refrigeration cycle.

The amount of liquid produced by the cooling of the head product of the column supplied to the ethylene refrigeration cycle is advantageously taken from the ethylene refrigeration cycle in gaseous state downstream of the ethylene compressor of the refrigeration cycle.

In accordance with the condensation conditions at the head of the column, the liquid produced by the cooling of the head product of the column is advantageously almost free from hydrogen and contains less methane than the gaseous head product of the column.

If necessary, parts of hydrogen and methane can be taken from the ethylene refrigeration cycle as inert gases which are afterwards preferably added to fraction A. Fraction B is therefore advantageously depleted, preferably in low boilers, in hydrogen and methane by removing them as inert gas from the refrigeration cycle. According to the present invention, the coupling of condensation of the overhead product of the separating column with the aid of the ethylene cooling circuit refrigeration cycle necessary for cooling allows advantageously the production of two grades of ethylene namely fraction A and fraction B.

The quantities defined below to characterize fraction A are advantageously those for fraction A containing the inert gases taken from the refrigeration cycle.

Fraction A advantageously contains more than 10, preferably more than 20 and more preferably more than 25% the ethylene quantity which is contained in the total of fraction A plus fraction B. Fraction A advantageously contains less than 90, preferably less than 80 and more preferably less than 75% the ethylene quantity which is contained in the total of fraction A plus fraction B.

Fraction A advantageously contains more than 80, preferably more than 85 and more preferably more than 90% the hydrogen quantity which is contained in the total of fraction A plus fraction B.

Fraction A advantageously contains more than 70, preferably more than 75 and more preferably more than 80% the methane quantity which is contained in the total of fraction A plus fraction B.

Fraction A advantageously contains less than 50, preferably less than 45 and more preferably less than 40% of the ethane quantity which is contained in the total of fraction A plus fraction B.

Fraction B is characterized by a content of compounds containing at least 3 carbon atoms, advantageously less than or equal to 0.1%, preferably less than or equal to 0.05% and in a particularly preferred manner less than or equal to 0.01% by volume relative to the total volume of fraction B.

Fraction C advantageously contains at least 95%, preferably at least 98% and particularly preferably at least 99% of compounds comprising at least 3 carbon atoms contained in the purified gas stream subjected to step d).

Fraction C advantageously contains at most 1%, preferably at most 0.8% and particularly preferably at most 0.5% by weight of ethylene relative to the total weight of fraction C.

Examples of product composition (wt %) are the following:

| | Raw material | | | |
| --- | --- | --- | --- | --- |
| | Ethane | | Mixture propane/butane | |
| Product | Fraction A | Fraction B | Fraction A | Fraction B |
| Hydrogen | 4.7 | 0.03 | 2.9 | 0.02 |
| Methane | 14 | 1.7 | 52 | 6 |
| Ethylene | 77.6 | 91.7 | 44.2 | 91 |
| Ethane | 3.7 | 6.6 | 0.9 | 3 |
| Propylene | <<1 ppm | <<1 ppm | <<1 ppm | <<1 ppm |

The heavy fraction generated in the bottom of the column (fraction C) contains advantageously ethane as well as hydrocarbons with three, four or five carbon atoms. Hydrocarbons with six or more carbon atoms being no longer contained in fraction C, this fraction can undergo hydrogenation without further treatment, preferably before being used as feedstock.

Fraction C is therefore preferable hydrogenated and fed to the hydrocarbon source in step a).

The technology of hydrogenation depends upon the feedstock for the ethylene production:

When using ethane as feedstock for ethylene production, fraction C contains mainly ethane, in addition to small amounts of ethylene and hydrocarbons with three of four carbon atoms. Before re-using the product as feedstock, high unsaturated compounds such as propyne, butadiene, vinyl acetylene are preferably removed, otherwise these substances lead to strong coke formation in the pyrolysis furnaces.

The hydrogenation of these strongly unsaturated compounds is more preferably made alongside with the hydrogenation acetylene in the selective hydrogenation which occurs preferably downstream of the compressor. This allows to recycle fraction C to the furnaces without further hydrogenation. If an additional hydrogenation is necessary, this is advantageously done as gas phase hydrogenation with known catalysts on the basis of palladium.

When using ethane as feedstock, the hydrogenation of fraction C takes therefore more preferably place together with the optional hydrogenation of acetylene allowing direct supply of fraction C to the feedstock without further hydrogenation.

When using propane and/or butane as feedstock for the ethylene production, larger amounts of propylene/butadiene accumulate as by-products in fraction C, together with the separated ethane. The hydrocarbons with six and more carbon atoms being already separated upstream of the separating column, it is therefore advantageously possible to hydrogenate fraction C without further treatment such as additional separation. The hydrogenation of fraction C is preferably done in adiabatic trickle phase reactors, more preferably with proven catalysts on the basis of palladium.

When using propane, butane or propane/butane mixtures as feedstock, fraction C is therefore most preferably subjected to hydrogenation in a trickle-phase reactor without additional separation and afterwards mixed with the feedstock.

In some cases, it can be interesting to isolate ethane as an individual fraction in order to valorize it. In these circumstances, the process according to the invention can be adapted so that ethane is isolated, for example by drawing it off as an individual fraction from the bottom of the distillation column used to isolate fraction C or by separating it from the heavier hydrocarbons present in fraction C by the use of a further distillation column. After having been recovered, ethane can be burnt as fuel or valorized chemically.

According to step f) of the process according to the invention, fraction A and fraction B are separately supplied to chemical use of ethylene.

Among the chemical use of ethylene, one may cite the manufacture of ethylene derivative compounds manufactured directly starting with ethylene such as for examples ethylene oxide, linear alpha-olefins, linear primary alcohols, homopolymers and copolymers of ethylene, ethylbenzene, vinyl acetate, acetaldehyde, ethyl alcohol, propionaldehyde and 1,2-dichloroethane and also of compound derived there from such as for examples glycols and ethers manufactured from ethylene oxide,
styrene manufactured from ethylbenzene and polymers of styrene derived from styrene,
vinyl chloride (VC) manufactured from 1,2-dichloroethane (DCE),
vinylidene chloride, fluorinated hydrocarbons and polyvinyl chloride (PVC) derived from VC and fluorinated polymers derived from fluorinated hydrocarbons, as well as
polyvinylidene chloride and fluorinated hydrocarbons (and fluorinated polymers) derived from vinylidene chloride.

Preferably, fraction A and fraction B are separately conveyed to the manufacture of at least one ethylene derivative compound.

The expression "at least one ethylene derivative compound" is understood to mean, for the purpose of the present invention, that one or more than one ethylene derivative compounds may be manufactured by the process according to the present invention.

The expression "ethylene derivative compound" is understood to mean, for the purpose of the present invention, any ethylene derivative compound manufactured directly starting with ethylene as well as any compound derived there from.

The expression "ethylene derivative compound manufactured directly starting with ethylene" is understood to mean, for the purpose of the present invention, any compound manufactured directly from ethylene.

The expression "compound derived there from" is understood to mean, for the purpose of the present invention, any compound manufactured from one compound itself manufactured from ethylene as well as any compound derived there from.

More preferably, one fraction among fraction A and fraction B is conveyed to the manufacture of 1,2-dichloroethane (DCE) and optionally of any compound derived there from, optionally after having been subjected to an acetylene hydrogenation, while the other fraction is conveyed to the manufacture of at least one ethylene derivative compound manufactured directly starting with ethylene which is different from 1,2-dichloroethane and optionally of any compound derived there from.

Most preferably, fraction A and fraction B are both conveyed to the manufacture of 1,2-dichloroethane and optionally of any compound derived there from, optionally after having been subjected to an acetylene hydrogenation.

A particular preferred process is the one in which fraction A is conveyed to a chlorination reactor and fraction B to an oxychlorination reactor, in which reactors most of the ethylene present in the fractions A and B is converted to 1,2-dichloroethane. The 1,2-dichloroethane obtained is afterwards advantageously separated from the streams of products derived from the chlorination and oxychlorination reactors, preferably subjected to a DCE cracking step to produce vinyl chloride (VC) which itself is afterwards more preferably polymerized to produce polyvinyl chloride (PVC).

A preferred embodiment of the process according to the invention is a process for the production of ethylene for chemical use starting with a hydrocarbon source according to which:
a) the hydrocarbon source is subjected to a first cracking step, namely a pyrolysis step carried out in a cracking oven, thus producing a mixture of cracking products;
b) the said mixture of cracking products is subjected to a succession of treatment steps, including a compression step, which makes it possible to obtain a purified crude gas stream;
c) the purified crude gas stream is then cooled to a temperature where hydrocarbons with 6 and more carbon atoms condense so that they can be removed from the purified crude gas stream and afterwards returned to step b);
d) the resulting purified gas stream is afterwards supplied to one separating column, where a fraction containing hydrogen, methane and ethylene (fraction A) is separated at the head of the column and a heavy fraction (fraction C) is separated at the bottom of the column;
e) a part of the reflux of this column is supplied to a refrigeration cycle which is an ethylene refrigeration cycle leading to a fraction enriched with ethylene (fraction B);
e') fraction B is optionally depleted in hydrogen and methane by removing them as inert gas from the refrigeration cycle;
e'') hydrogen and methane are optionally added to fraction A;
f) fraction A and fraction B are separately supplied to chemical use of ethylene;
g) fraction C is hydrogenated and fed to the hydrocarbon source in step a).

The process according to the invention will now be illustrated with reference to the drawing accompanying the present description. This drawing consists of the appended FIG. 1, schematically representing the preferred embodiment of the process according to the invention.

The hydrocarbon source (a) is subjected to a first cracking step (1), where it is converted into a mixture of cracking products. The mixture of cracking products is afterwards subjected to a succession of treatment steps (2) including a compression step (called hereafter compressor area) in order to obtain a purified crude gas stream (b). The purified crude gas stream (b) is then cooled in (3), so that the hydrocarbons with six and more carbon atoms condense, before being returned to the compressor area (2). The resulting purified gas stream (c) is afterwards separated in the column (4) into (d) at the head of the column and into (j) at the bottom of the column (fraction C). Fraction (d) containing ethylene, methane, hydrogen as well as traces of CO is then partly condensed in the condenser (5) by means of liquid ethylene (i) from the ethylene refrigeration cycle (6). The remaining gas phase (e)

is supplied to chemical use of the ethylene contained therein (fraction A). The condensed liquid head product (f) is used as reflux to the column, part (g) is given to the ethylene refrigeration cycle (6) and, after the recovery of the contained cold energy, given in gaseous state as (e') (fraction B) to chemical use of the contained ethylene. If necessary, dissolved hydrogen as well as methane are separated as inert gas (h) in the ethylene refrigeration cycle. The inert gases (h) may be added to (e).

The bottom product (j) of column (4) contains ethane as well as hydrocarbons with 3 to 5 carbon atoms. The hydrogenation of unsaturated components contained therein takes place in the hydrogenation (7). The hydrogenated product (k) is added to the feedstock (a) prior to cracking (1).

The invention claimed is:

1. A process for the production of ethylene for chemical use starting with a hydrocarbon source according to which:
    a) the hydrocarbon source is subjected to a first cracking step, namely a pyrolysis step carried out in a cracking oven, thus producing a mixture of cracking products;
    b) said mixture of cracking products is subjected to a succession of treatment steps, including a compression step, which makes it possible to obtain a purified crude gas stream;
    c) the purified crude gas stream is then cooled to a temperature where hydrocarbons with 6 and more carbon atoms condense so that they can be removed from the purified crude gas stream;
    d) the resulting purified gas stream is afterwards supplied to one separating column, where a fraction A containing hydrogen, methane and ethylene is separated at the head of the column and a heavy fraction C is separated at the bottom of the column;
    e) a part of the reflux of this column is supplied to a refrigeration cycle leading to a fraction B enriched with ethylene; and
    f) said fraction A and said fraction B are separately supplied to chemical use of ethylene.

2. The process according to claim 1, wherein the hydrocarbon source is selected from the group consisting of naphtha, gas oil, natural gas liquid, ethane, propane, butane, isobutane and mixtures thereof.

3. The process according to claim 2, wherein the hydrocarbon source is selected from the group consisting of ethane, propane, butane, and propane/butane mixtures.

4. The process according to claim 1, wherein the hydrocarbons condensed in step c) are returned to step b).

5. The process according to claim 1, wherein the refrigeration cycle is an ethylene refrigeration cycle.

6. The process according to claim 1, wherein the part of the reflux of the separating column is supplied to the refrigeration cycle after evaporation and utilization of the refrigeration content.

7. The process according to claim 1, wherein said fraction B is depleted in hydrogen and methane by removing them as inert gas from the refrigeration cycle.

8. The process according to claim 1, wherein said fraction C is hydrogenated and fed to the hydrocarbon source in step a).

9. The process according to claim 8, wherein, when using ethane as feedstock, the hydrogenation of said fraction C takes place together with the optional hydrogenation of acetylene allowing direct supply of said fraction C to the hydrocarbon source without further hydrogenation.

10. The process according to claim 8, wherein, when using propane, butane or propane/butane mixtures as feedstock, said fraction C is subjected to hydrogenation in a trickle-phase reactor without additional separation and afterwards mixed with the hydrocarbon source.

* * * * *